United States Patent [19]

Tarabichy et al.

[11] Patent Number: 4,702,236
[45] Date of Patent: Oct. 27, 1987

[54] REVISION ARTHROPLASTY METHOD AND RELATED INSTRUMENT

[76] Inventors: Samih Tarabichy, 5360 Patricia, #14, Montreal, Quebec, Canada, H4V 1Z2; Barry Miller, 211 Drakes Bay, Los Gatos, Calif. 95030

[21] Appl. No.: 869,259
[22] Filed: Jun. 2, 1986
[51] Int. Cl.$^4$ .............................................. A61F 5/04
[52] U.S. Cl. ............................... 128/92 V; 128/92 VP
[58] Field of Search ........... 128/92 R, 92 VP, 92 VQ, 128/92 V, 92 VM, 92 VJ

[56] References Cited

U.S. PATENT DOCUMENTS

| | | | |
|---|---|---|---|
| 3,626,935 | 12/1971 | Pollock | 128/92 VT |
| 4,399,813 | 8/1983 | Barber | 128/92 VT |
| 4,612,922 | 9/1986 | Barber | 128/92 R |

Primary Examiner—C. Fred Rosenbaum
Assistant Examiner—C. W. Shedd

[57] ABSTRACT

A method for revision arthroplasty for the removal of a loosened or defective prosthesis component anchored in a polymer cement set in a bone cavity. The method comprises exposing and disconnecting, if necessary, a connecting free end portion of the prosthesis component at an extremity of the bone cavity. The loosened or defective prosthesis is then removed out of the bone cavity from the extremity thereof. The cement is then removed from the cavity by the use of an instrument having a heated working end which is heated to a temperature exceeding the melting point of the cement whereby cement can be removed without perforating or damaging the bone.

3 Claims, 6 Drawing Figures

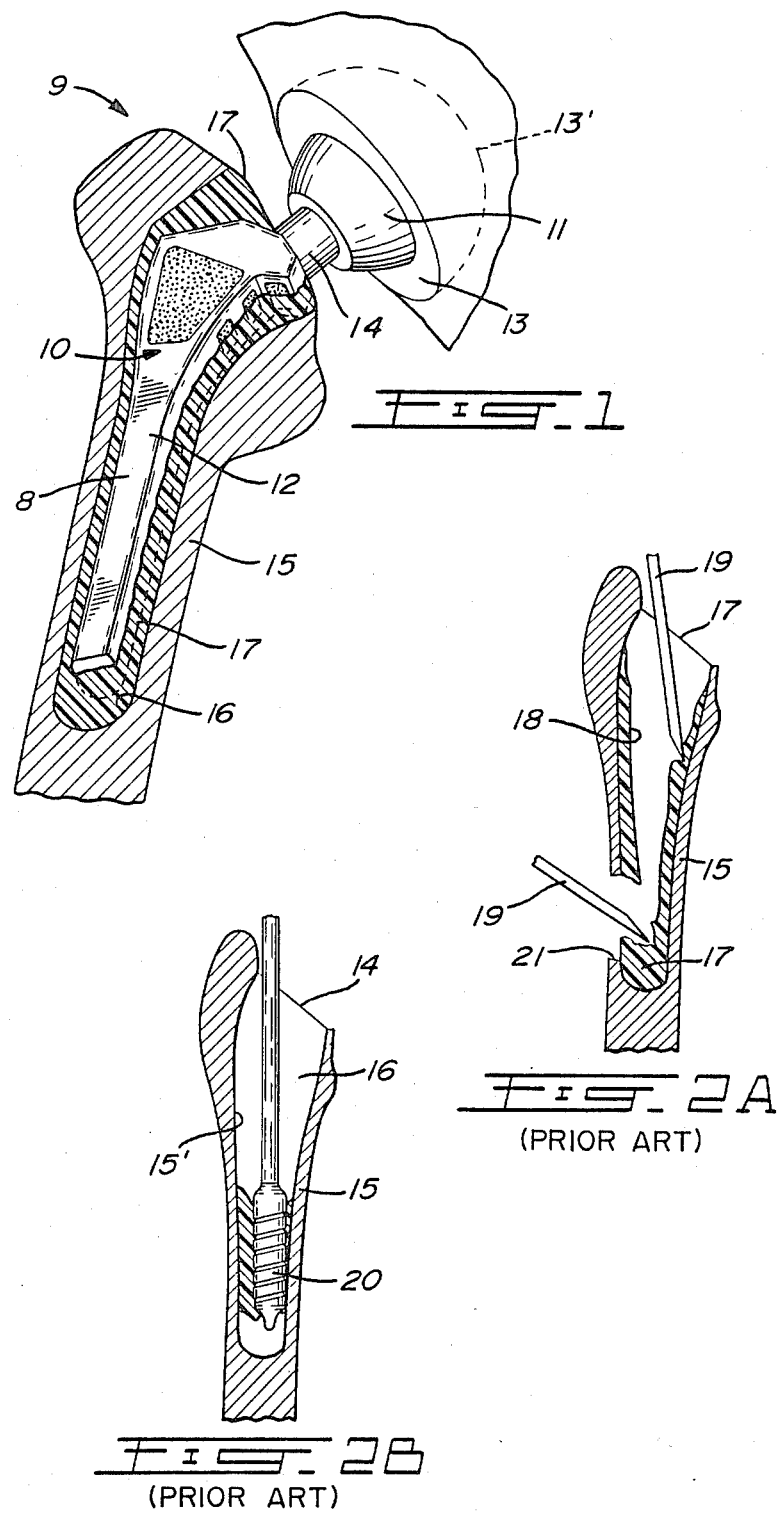

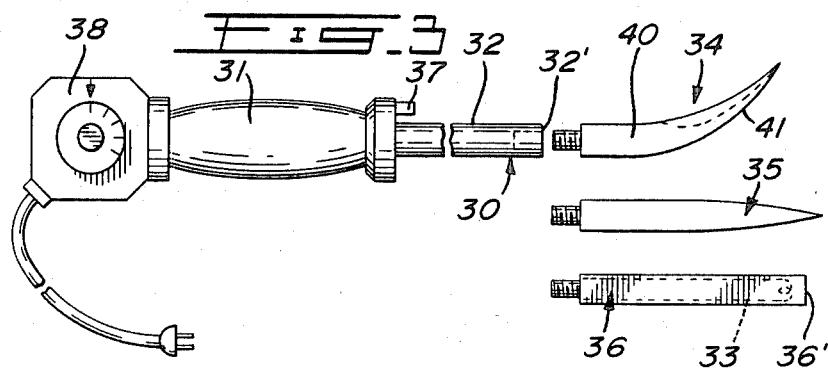
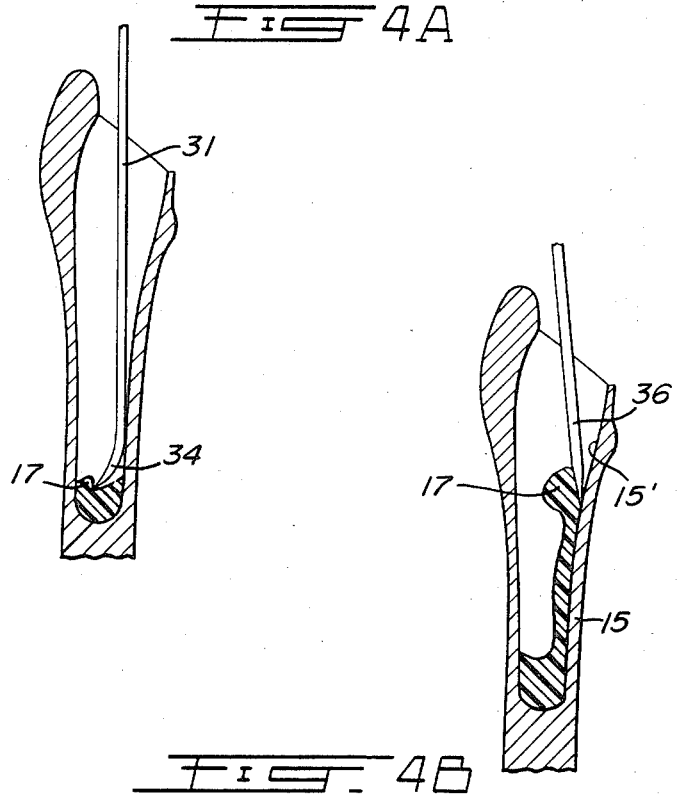

REVISION ARTHROPLASTY METHOD AND RELATED INSTRUMENT

BACKGROUND OF INVENTION

1. Field of Invention

The present invention relates to a method and an instrument for revision arthroplasty for the removal of thermoplastic polymer cement set in a bone cavity after the loosened or defective prosthesis component is removed from its anchoring in the cement. More specifically, but not exclusively, the present method applies to the removal of polymethylmethacrylate cement casted in a femur cavity.

2. Description of Prior Art

It is common practice, in revision arthroplasty, to utilize chisels and hammers as well as high speed turbine drills in order to remove set thermoplastic polymer cement which is embedded in a bone cavity to secure a prosthesis component therein. This cement is usually removed by chiselling at the cement from the neck of the bone cavity after the prosthesis component has been dislodged from the cement. It is possible to insert instruments through this cavity and chisel away at the wall of the cement. A problem with this method is that often whilst chiselling away, a piece of the bone will be cut away or break off by the impact of the chisel. A further method is to insert a drill bit through the neck of the bone cavity and again, the cutting edges of the drill will often penetrate or scrape off portions of the bone. The reason for this is that the surgeon is unaware of how close the bone wall is to the inner cement wall being worked on.

It is often necessary, particularly in order to remove this plastic cement from the bottom of the bone cavity, to make a window or gutter or hole in the bone side wall by the use of a drill and to chip at the cement through this window. Again, because these drills are high speed and have sharp cutting elements, often the bone is penetrated through, thus damaging and weakening the bone. Another disadvantage of the prior art methods is that it is often difficult to remove all of the cement from the bone cavity and often loose chips may remain within the cavity.

There are other disadvantages of these prior art methods. For example, the high speed turbine drills are extremely costly, and they generate a fine powder while drilling through the hardened cement and this powder dirties the area around the incision making it more difficult to work and disinfect. These prior art methods are also very time-consuming and the devices are bulky and difficult to handle.

A common revision arthroplasty relates to the hip joint femoral prosthesis where an estimated 20,000 revisions are effected annually and such revisions are on the increase.

SUMMARY OF THE INVENTION

It is a feature of the present invention to provide a new method for revision arthroplasty and an instrument for the removal of the thermoplastic polymer cement from the bone cavity.

Another feature of the present invention is to provide a novel method for revision arthroplasty which is simple, requires substantially less time than prior art methods and which is safe and does not damage the bone.

Another feature of the present invention is to provide an instrument for the removal of thermoplastic polymer cement from a bone cavity and which instrument is economical, easy to use, and does not damage the bone structure and which is capable of removing substantially all of the cement bonded to the wall of the bone cavity without damage to the wall or without requiring the formation of apertures within the bone, thereby maintaining the bone substantially unaffected by the replacement of the prosthesis component and anchoring cement.

According to the above features, from a broad aspect, the present invention provides a method for the removal of thermoplastic polymer cement set in a bone cavity after a loosened or defective prosthesis component anchored in the cement has been removed. The method comprises the steps of exposing and dislocating, if necessary, a connecting free end portion of the prosthesis component and an extremity of the bone cavity. The loosened or defective prosthesis component is then removed out of the bone cavity from the extremity of the bone. The cement is then removed from the cavity by the use of an instrument having a heated working end heated to a temperature exceeding the melting point of the cement whereby the cement can be removed without perforating or damaging the bone.

According to a further broad aspect of the present invention, there is provided an instrument for the removal of thermoplastic polymer cement used for anchoring a prosthesis component in a bone cavity. The instrument comprises a handle having a working element removably secured thereto. The working element has a shaped working end of heat conductive material for effecting a predetermined cement removal function. A resistive heating element is embedded in the free end.

BRIEF DESCRIPTION OF DRAWINGS

A preferred embodiment of the present invention will now be described with reference to the example thereof as illustrated in the accompanying drawings in which:

FIG. 1 is a fragmented, partly sectioned, perspective view showing a femoral prosthesis forming a hip joint and as is conventional in the prior art;

FIGS. 2A and 2B are section views showing a free end portion of the femur bone whereby to illustrate prior art methods of removing thermoplastic polymer cement from a cavity made from the femoral neck of the bone;

FIG. 3 is a side view showing the thermoplastic polymer removing instrument of the present invention and illustrating different working ends; and FIGS. 4A and 4B are section views illustrating the removal of the thermoplastic polymer cement by the use of the tool shown in FIG. 3.

DESCRIPTION OF PREFERRED EMBODIMENTS

Referring now to the drawings, and more particularly to FIG. 1, there is shown the manner in which a total hip prosthesis 9 is secured to the hip joint. As hereinshown, the total hip prosthesis 9 comprises a cup component 13 and a femoral component 10. The cup component 13 is secured within the acetabular cavity 13' which is filled with a thermoplastic polymer cement (not shown) and pushed therein with the cup component oriented in a substantially precise axis whereby to receive the connecting head 11 of the femoral component 10 which is anchored within the femur bone 15.

In order to anchor the femoral component 10 within the femur bone 15, a cavity 16 is drilled out of the bone from the femoral neck free end 17 after the joint has been dislocated to provide access to the femoral neck free end 17. This cavity is then filled or partly filled with a thermoplastic polymer cement, and usually polymethylmethacrylate which has a melting point of about 130° C. which is mixed and injected in the cavity by means of a syringe and pushed therein under pressure whereby to completely fill the cavity whereby when the stem 8 of the femoral component 10 is inserted within the cavity, all of the areas of the cavity are filled with the cement to provide for a rigid anchor once the cement has set and hardened.

Often, it is necessary to repair the femoral prosthesis due to one of the components becoming loose and more often, the femoral component. This loosening may be due to various causes such as prolonged wear in the femoral neck area, infection in the bone cavity thus losing the adherence of the cement by fluid escaping in the area between the wall of the bone and the cement, or by damage due to injury. When such component has to be replaced or re-anchored, it is necessary to make an incision in the patient to expose the joint and to dislocate the connecting head 11 of the femoral component from the cup component 13 and to displace the femoral bone for access to the femoral neck.

In the prior art method heretofore known, any cement 18 in the femoral neck area was then chipped away by means of a chisel and hammer and the femoral component was then yanked out of the femur cavity 16 or drilled out of the cavity. After the femoral component 12 was removed, the cement 18 was then chiselled away as shown in FIG. 2A either through the femoral neck free end 17 or by making a window or gutter 21 in the bone 15. As shown in FIG. 2A, these chisels 19 are provided with sharp scraping ends and often damage the inside wall 15' of the femur 15. Also, when penetrating through the window 21, any sharp blow could fracture the bone as the force is applied at an angle to the long axis of the bone and often transverse thereto.

FIG. 2B shows another prior art method of removing the cement from the bone cavity 16. As herein shown, a drill bit 20 from a high speed drill is inserted through the femoral neck 17 and the cement is drilled out. The disadvantages of this method are explained in the preamble portion of the specification and as can be seen, the end of the drill bit 20 often penetrates through the cement and removes further bone particles thus expanding the cavity 16 and weakening the side wall of the bone. Also, in certain cases, the drill bit penetrates through the bone wall causing fracture or considerably weakening the bone.

Referring now to FIG. 3, there is shown the instrument of the present invention which is utilized to remove the cement from the bone cavity. The instrument comprises an elongated working element 30 which is secured to a handle 31. A shaped working end 40 of heat conductive metal is removably secured to the working element body 32 and has a resistive heating element 33 embedded therein whereby to heat the free end portion 41 thereof to a temperature exceeding the melting point of the cement 18 whereby to melt it away from the bone cavity wall.

The working free end may have various shapes depending on the configuration of the particular bone configurations and as shown in FIG. 3, may be shaped as a spoon 34 which extends at a suitable angle, herein 45°. Other spoons may be provided extending at angles of 90° and 70° to scrape the side walls of the cavity.

In order to make a pilot hole in the cement without perforating the cortex, prior to melt-scraping or melt-scooping it, there may be proivded a working end having the shape of a pin 35. Additionally, a working end may be provided as a chesel or knife 36 with the free end 36' thereof being formed as a sharp blade end. Such an element is shown in FIG. 4B and used for scraping the cement 18 from the side wall 15' of the femur bone 15. As shown in FIG. 4A, the spoon-shaped end 34 is utilized to scrape out the cement on the side wall or the bottom end of the cavity.

It is pointed out that with the instrument of the present invention, it is only necessary to apply limited pressure against the cement and let the tool work in the cement by melting it. When the tip end of the working end of the instrument touches the bone, it ceases the advance or penetrates through the cement as the bone will not melt at the working temperature of the instrument. Accordingly, the surgeon is aware that he has touched the side wall of the bone.

In order to provide more visibility while effecting this cement removal, a light source 37, such as a fiber optic light, may be positioned at the end of the handle 31 and aligned with the shaft 32 whereby to direct light toward the working end 41 of the working element 40. However, it is pointed out that even if a portion of the cavity is not visible by the surgeon, the fact that the instrument can melt the cement and scrape it off the bone side wall is sufficient to effect substantially complete removal of the cement by a scraping action against the side wall of the bone cavity without damaging the bone.

As shown in FIG. 3, the handle 31 may also be provided with a variable resistive control device 38 whereby to vary the current flowing through the resistive heating element to regulate the temperature thereof and depending on the type of cement used and the melting point thereof. It is customary in such implants, to utilize polymethylmethacrylate which has a melting point of about 130° C. and the temperature of the working end of the instrument is usually heated to temperatures in the range of 150° to 200° C. Bone cement is also usually a poor heat conductor to protect the bone from damage by heat when pouring the hot cement within the bone cavity. The heat conduction of bone cement is usually 0.0004 cal per centimeter square per centimeter per second per ° C. while the heat conductivity of the bone is 0.0009. For comparison purposes, the heat conductivity of aluminum is 0.563. This bone cement usually polymerizes (hardens) at temperature in the range of 80° to 128° C.

In experiments conducted with tools constructed in accordance with the present invention, it was observed that three centimeters of bone cement could be penetrated with a straight point end tip, as shown at 35 in FIG. 3, in approximately 10 seconds and it was noted that this tip would no longer advance its penetration when it touched the bone cortex.

Although in FIG. 3 the working end 40 is shown as being removable from the working element portion 32, it could be manufactured as a single part which is entirely removable from the handle 31. Also, the part 32 may be made of an insulating material having electrical contacts at its connecting end 32' whereby to complete the electric circuit to the resistive element 33 embedded within the working end 31. Alternatively, the outer surface of the working element 30 may have an insulating coating or covering and exposing only the working end 41.

As can be seen, the method of effecting a revision arthroplasty utilizing the instrument of the present invention has various advantages over the prior art and namely, is easy to use, economical, does not damage the bone, does not require drilling windows in the bone, can work in difficult areas of the bone cavity without visual access thereto, and results in a faster revision which reduce surgical complication.

It is within the ambit of the present invention to cover any obvious modifications of the preferred embodiments of the present invention described herein, provided such modifications fall within the scope of the appended claims.

We claim:

1. A method for the removal of thermoplastic polymer cement set in a bone cavity after a loosened or defective prosthesis component previously anchored in the thermoplastic cement has been removed from the bone cavity, said method comprising the step of:
   (i) removing cement from said cavity by the use of instruments having a heated working end heated to a temperature exceeding the melting point of said cement whereby cement can be removed without perforating or damaging the bone.

2. A method as claimed in claim 1 wherein before step (i) there is provided the steps of:
   (a) exposing and disconnecting, if necessary, a connecting free end portion of said prosthesis component from an exposed end of said bone cavity; and
   (b) removing said loosened or defective prosthesis component out of said bone cavity from said exposed end.

3. A method as claimed in claim 1 wherein said step (i) comprises selecting a working element having a desired shape to effect said excavation of said cement, penetrating said instrument in said cement by melting the cement until the penetration is arrested by the wall of the bone thereby removing substantially all of said cement necessary for re-anchoring said removed prosthesis component or a new prosthesis in new cement inserted into a cleaned bone cavity undamaged by the excavation procedure.

* * * * *